United States Patent [19]
Koeller

[11] Patent Number: 6,080,565
[45] Date of Patent: Jun. 27, 2000

[54] CUTINASES AS INDUCERS OF PLANT DEFENSE REACTIONS AND AGENTS FOR THE CONTROL OF PLANT DISEASES

[75] Inventor: Wolfram D. Koeller, Geneva, N.Y.

[73] Assignee: Cornell Research Foundation, Inc., Ithaca, N.Y.

[21] Appl. No.: 08/920,241

[22] Filed: Aug. 28, 1997

Related U.S. Application Data

[60] Provisional application No. 60/025,443, Sep. 4, 1996.
[51] Int. Cl.[7] ................................................ C12N 9/02
[52] U.S. Cl. ...................... 435/196; 435/197; 435/198; 504/117; 424/94.6; 800/200
[58] Field of Search ..................................... 435/196, 197, 435/198; 800/200; 504/117; 424/94.6

[56] References Cited

U.S. PATENT DOCUMENTS

| | | |
|---|---|---|
| 4,762,547 | 8/1988 | Iwasaki et al. . |
| 5,019,411 | 5/1991 | Johnson et al. . |
| 5,037,662 | 8/1991 | Poulose et al. . |
| 5,298,265 | 3/1994 | Poulose et al. . |

FOREIGN PATENT DOCUMENTS 61-178907   1/1985   Japan .

*Primary Examiner*—Leon B. Lankford, Jr.
*Attorney, Agent, or Firm*—Nixon Peabody LLP

[57] ABSTRACT

The present invention relates to the use of esterases as control agents of plant diseases. The esterases are applied to the cells of a plant under conditions effective to impart resistance to plant diseases without decomposing waxy surface layers of the plant.

19 Claims, 4 Drawing Sheets

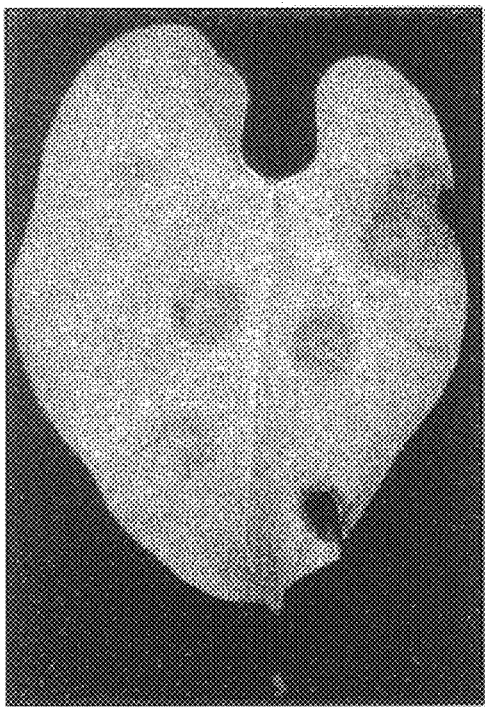 
FIG. 1A
FIG. 1B

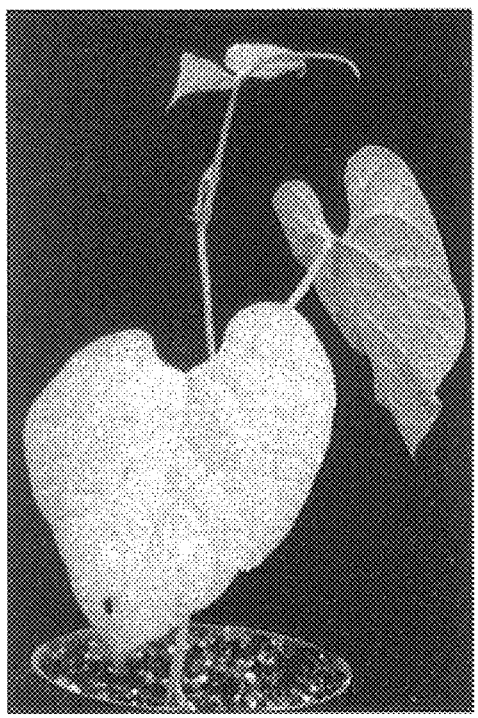 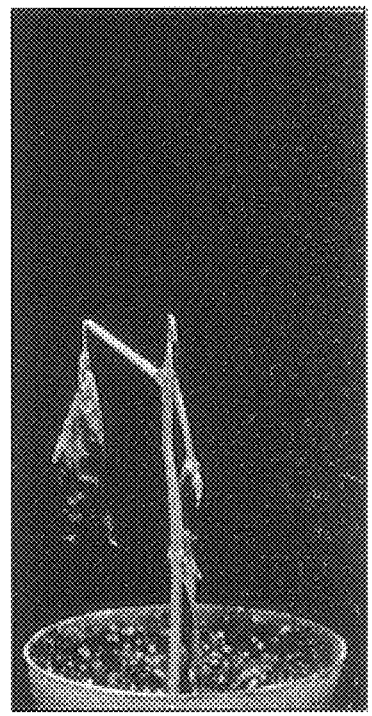
*FIG. 2A*        *FIG. 2B*

CUTINASES AS INDUCERS OF PLANT DEFENSE REACTIONS AND AGENTS FOR THE CONTROL OF PLANT DISEASES

This application claims benefit of Provisional application Ser. No. 60/025,443, filed Sep. 4, 1996.

FIELD OF THE INVENTION

The present invention relates to a novel biological activity of esterases as triggers of plant defenses. More specifically, the present invention relates to the activity of esterases as inducers of plant defenses against pathogens and their use as plant disease control agents.

BACKGROUND OF THE INVENTION

The epidermis of aerial plant tissues is covered by the hydrophobic cuticle, a two-component material consisting of plant waxes and the polymer cutin. The polyester cutin is composed of esterified ω-hydroxyfatty acids (Kolattukudy, P. E., Espelie, K. E., and Soliday, C. L. 1981. Hydrophobic layers attached to cell walls. Cutin, suberin and associated waxes. Pages 225–254 in: Plant Carbohydrates II—Extracelluar Carbohydrates. W. Tanner and F. A. Loewus, eds. Springer Verlag, Berlin).

Cutinases are defined as esterases with cutin-hydrolytic activities (Köller, W. 1991. The plant cuticle: A first barrier to be overcome by fungal plant pathogens. Pages 219–246 in: The Fungal Spore and Disease Initiation in Plants and Animals. G. T. Cole and H. C. Hoch, eds. Plenum Press, New York). Mostly produced by microorganisms, cutinases are involved in the saprophytic degradation of leaf cuticles by soil organisms (Stahl, D. J., and Schäafer, W. 1992. Cutinase is not required for fungal pathogenicity on pea. Plant Cell 4; 621–629, Köller, W., Yao, C., Trail, F., and Parker, D. M. 1995. Role of cutinases in the invasion of plants. Can. J. Bot. 73 (Suppl.1): S1109–S1118.) and in the penetration of plant cuticles during early steps of plant infection, primarily by plant pathogenic fungi (Köller, W. 1991. The plant cuticle: A first barrier to be overcome by fungal plant pathogens. Pages 219–246 in: The Fungal Spore and Disease Initiation in Plants and Animals. G. T. Cole and H. C. Hoch, eds. Plenum Press, New York; Köller, W., Parker, D. M., and Becker, C. M. 1991. Role of cutinase in the penetration of apple leaves by *Venturia inaequalis*. Phytopathology 81: 1375–1379).

The enzymatic activity of cutinases is not restricted to cutin hydrolysis. Cutinases have been shown to act as lipases, and some lipases also hydrolyze cutin (Martinez, C., Nicolas, A., van Tilbeurgh, H., Egloff, M.-P., Cudrey, C., Verger, R., and Cambillau, C. 1994. Cutinase, a lipolytic enzyme with a preformed oxyanion hole. Biochemistry 33, 83–89; Gérard, H. C., Fett, W. F., Osman, S. F., and Moreau, R. A. 1993. Evaluation of cutinase activity of various industrial lipases. Biotechnol. Appl. Biochem 17: 181–189).

Cutinases and lipases belong to the enzyme class of esterases (Köller, W., and Kolattukudy, P. E. 1982. Mechanism of action of cutinase: Chemical modification of the catalytic triad characteristic for serine hydrolases. Biochemistry 21: 3083–3090; Derewenda, Z. S., and Sharp, A. M. 1993. News from the interface: The molecular structures of triacylglyceride lipases. Trends Biochem. Sci 18: 20–25), together with the large family of non-specific caboxylesterases with broad substrate specificities (e.g.; Aida, K., Moore, R., and Negishi, M. 1993. Cloning and nucleotide sequence of a novel male-predominant carboxylesterase in mouse liver. Biochim. Biophys. Acta 1174: 72–74). All esterases including cutinases, lipases and non-specific carboxylesterases hydrolyze chromogenic model esters such as acyl esters of p-nitrophenol (Huggins, C., and Lapides, J. 1947. Chromogenic substrates. IV. Acyl esters of p-nitrophenol as substrates for the colorimetric determination of esterase. J. Biol. Chem. 170: 467–482).

Esterases such as lipase and cutinase have been shown to improve the biological effect of fungicides and other pesticides by decomposing the waxy layers (=cuticles) of plants (Iwasaki, T., and Hioki, Y. 1988. Enhancement of biocide. U.S. Pat. No. 4,762,547).

The sole activity of esterases as inducers of plant defense reactions and, therefore, as sole agents for plant disease control with a mode of action not relating to an enhancement of fungicide efficacies has never been described. Utilization of esterases for the control of plant diseases would provide a non-toxic and environmentally benign means of plant protection and, thus, would be of great importance to agriculture.

SUMMARY OF THE INVENTION

Accordingly, the object of the present invention is to demonstrate that esterases are active as control agents of plant diseases by inducing plant defenses against microbial pathogens.

The object has been attained by treating leaves of beans and grapevines with typical esterases as defined by their activity of hydrolyzing the model esterase substrate p-nitropenyl butyrate (Huggins, C., and Lapides, J. 1947. Chromogenic substrates. IV. Acyl esters of p-nitrophenol as substrates for the colorimetric determination of esterase. J. Biol. Chem. 170: 467–482), infecting the treated leaves with three different pathogenic fungi [grapevine leaves with *Guignardia bidwellii* (Ellis) Viala & Ravaz, bean leaves with *Rhizoctonia solani* Kühn and *Sclerotinia sclerotiorum* (Lib.) de Bary], and recording disease symptom development on cutinase-treated leaves in comparison with untreated control leaves. In all three cases, treatment with esterases prevented the development of disease symptoms in the absence of any fungicide.

The lack of cuticle decomposition at active esterase concentrations as a factor contributing to disease control was shown by studying the uptake of a cuticle impermeable compound through untreated and esterase-treated leaf cuticles. The action of esterases as triggers of plant defense reactions was shown by the lack of direct effects of on the growth of pathogens and by the appearance of necrotic lesions at sites of inoculation.

The present invention provides a novel agent for the the control of plant diseases by inducing plant defense reactions.

BRIEF DESCRIPTION OF THE DRAWINGS

FIGS. 1A and 1B show symptoms of web blight on bean leaves 2 days after infection. FIG. 1A shows nontreated control. FIG. 1B shows cutinase-treated.

FIGS. 2A and 2B show symptoms of web blight on bean leaves 6 days after infection. FIG. 2A shows cutinase-treated. FIG. 2B shows nontreated control.

DETAILED DESCRIPTION OF THE INVENTION

Figure 3B:
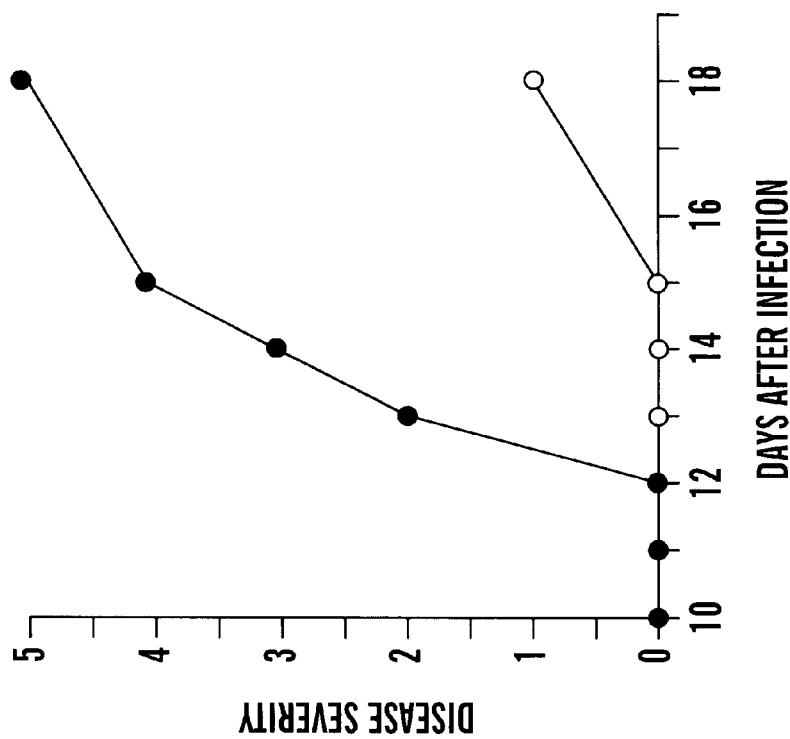
FIGS. 3A and 3B show the development of black rot on nontreated grape leaves (closed symbols) and on leaves treated with cutinase (closed symbols). A; LEAF 14; B; LEAF 15. Disease severity was rated as follows: 0=no lesions; 1=<¼ leaf covered; 2=¼ leaf covered; 3=<½ leaf covered; 4=½ leaf covered; 5=>⅔ leaf covered.

For the purpose of this invention, esterases are defined as enzymes that hydrolyze acyl esters of p-nitrophenol such as p-nitrophenyl butyrate (Huggins, C., and Lapides, J. 1947. Chromogenic substrates. IV. Acyl esters of p-nitrophenol as substrates for the calorimetric determination of esterase. J. Biol. Chem. 170: 467–482; Trail, F., and Köller, W. 1993. Diversity of cutinases from plant pathogenic fungi: Purification and characterization of two cutinases from *Alternaria brassicicola*. Physiol. Molec. Plant Pathol. 42: 205–220). Respective enzyme assays were performed as described before (Köller, W., and Parker, D. M. 1989. Purification and characterization of cutinase from *Venturia inaequalis*. Phytopathology 79: 278–283).

The sources of esterases were as follows:
a) Cutinase.

For the purpose of this invention, cutinase produced by *Venturia inaequalis* represents a typical cutinase, defined as esterase with cutinolytic activity. The respective enzyme was characterized as cutinase (Köller, W., and Parker, D. M. 1989. Purification and characterization of cutinase from *Venturia inaequalis*. Phytopathology 79: 278–283).

The cutinase from *Venturia inaequalis* according to the present invention can be obtained from culture fluids of the fungus cultivated in the presence of purified apple cutin. Cultivation conditions and a procedure for the purification of the enzyme was described in detail (Köller, W., and Parker, D. M. 1989. Purification and characterization of cutinase from *Venturia inaequalis*. Phytopathology 79: 278–283).
b) Lipases.

For the purpose of this invention, the industrial lipases PS and AK produced by Pseudomonas spp. were obtained from Amano International Co., Troy, Va., U.S.A. Both lipases were reported to also exhibit cutinolytic activities (Gerard, H. C., Fett, W. F., Osman, S. F., and Moreau, R. A. 1993. Evaluation of cutinase activity of various industrial lipases. Biotechnol. Appl. Biochem 17: 181–189).
c) Non-specific Carboxylesterase.

For the purpose of this invention, the pork liver carboxylesterase (E. C. 3.1.1.1) was purchased from Sigma Co., St. Louis, Mo.).

The embodiment of the present invention is the provision of inducing plant defense reactions and controling diseases by the application of esterases to the surfaces of plants challenged by plant pathogenic fungi. More specifically, the method of controlling diseases with esterases requires a solution containing cutinase at appropriate concentrations and detergents or surfactants such as Tween 20.

EXAMPLES

The invention will now be described by reference to specific examples. However, the invention is not be construed as being limited to the examples.

Example 1

Control of Web Blight with Cutinase

Web blight of beans is caused by *Rhizoctonia solani* Kühn and affects all aerial parts of beans. (R. Hall, ed. 1991. Compendium of Bean Diseases, APS Press, St. Paul). Bean plants (*Phaseolus vulgaris* L. cv. Bush Blue Lake) were grown for 10 days in growth chambers at 25 C. Infection of primary leaves with *Rhizoctonia solani* was done according to a published procedure. (Galindo, J. J., Abawi, G. S., and Thurston, H. D. 1982. Variability among isolates of *Rhizoctonia solani* associated with snap bean hypocotyls and soils in New York. Plant Disease 66: 390–394; Trail, F., and K öller, W. 1990. Diversity of cutinases from plant pathogenic fungi: Evidence for a relationship between enzyme properties and tissue specificity. Phyisol. Molec. Plant Pathol. 36: 495–508).

A mycelial suspension was prepared from 3-day-old cultures of *Rhizoctonia solani* AG1 (isolate obtained from Dr. G. S. Abawi, Cornell University) growing on potato dextrose agar by suspending mycelium from a single culture plate in 3 ml water containing 0.1% (v/v) Tween 20 and grinding in a glass tissue homogenizer.

Excised bean leaves were placed on grids in plastic boxes containing water, and 6 infection droplets per leaf (0.01 ml of mycelial suspension described above) were placed on the upper leaf surfaces (=nontreated). For treatments with cutinase, the infection droplets were supplemented with cutinase (=cutinase-treated). The boxes were closed, and disease symptoms were evaluated 48 h after inoculation and incubation at 25 C.

Typical round and rapidly expanding lesions developed on nontreated leaves. In the presence of cutinase (0.05 mg/ml), small, brown necrotic lesions became visible (FIG. 1). Disease symptoms did not develop from these necrotic lesions.

Necrosis of infected plant tissue as the consequence of rapid cell death is the typical symptom for a hypersensitive reaction, which is viewed as one of the primary mechanisms of plant resistance to infection by microbial pathogens (Goodman, R. N., and Novacky, A. J. 1994. The hypersensitive Reaction in Plants to Pathogens. APS Press, St. Paul, pp.244). The necrotic lesions caused by exposure of inoculation sites to cutinase suggested the induction of a resistance response of bean leaves to the pathogen as cause for disease control.

This resistance-inducing mode of action of cutinase was substantiated by the lack of any direct action of cutinase on the growth of the pathogen *Rhizoctonia solani*. Droplets of mycelial fragments of the pathogen containing cutinase at concentrations active in disease control were microscopically examined after 48 h of exposure. There was no inhibition or distortion of growth caused by cutinase in comparison to infection droplets containing no cutinase.

The cutinase dose required for the control of web blight on bean leaves is described in Table 1. Under the test conditions employed, a cutinase concentration of 0.01 mg/ml was sufficient for full control of the disease.

TABLE 1

Development of web blight lesions on bean leaves infected with droplets containing mycelial fragments of *Rhizoctonia solani*, 0.1% Tween 20, and various amounts of cutinase.

| Cutinase concentration (mg/ml) | Lesion diameter[a] (mm) |
|---|---|
| 0 | 75 |
| 0.001 | 76 |

TABLE 1-continued

Development of web blight lesions on bean leaves infected
with droplets containing mycelial fragments of Rhizoctonia solani,
0.1% Tween 20, and various amounts of cutinase.

| Cutinase concentration (mg/ml) | Lesion diameter[a] (mm) |
|---|---|
| 0.005 | 10 |
| 0.010 | 0[b] |
| 0.050 | 0[b] |

[a]Mean of 20 inoculation sites.
[b]Small necrotic lesions.

Cutinase at the fully active concentration of 0.01 mg/ml according to Table 1 also prevented the development of web blight in whole-plant experiments. Primary leaves of beans were drop-inoculated as described above, the plants were enclosed in plastic bags and incubated in a growth chamber for 6 days. No symptoms developed on the cutinase-treated plant, whereas the nontreated plant had died (FIG. 2).

Example 2

Control of Web Blight with Esterases

The cutinase employed in Example 1 is a highly active esterase as indicated by the rapid hydrolysis of the general esterase substrate p-nitropenhyl butyrate (Köller, W., and Parker, D. M. 1989. Purification and characterization of cutinase from *Venturia inaequalis*. Phytopathology 79: 278–283). In addition, esterases active as lipases with biological activities in the hydrolysis of triglycerides were reported to be also active as cutinases (Gérard, H. C., Fett, W. F., Osman, S. F., and Moreau, R. A. 1993. Evaluation of cutinase activity of various industrial lipases. Biotechnol. Appl. Biochem 17: 181–189).

Experiments were conducted to investigate, whether the esterase or the cutinase activities of lipases and cutinase were responsible for the control of web blight. A nonspecific carboxylesterase from porcine liver without a reported lipase or cutinase activity was included in the experiment. The results are summarized in Table 2.

The esterases employed at the protein concentration (10 μg/ml) of the fully active cutinase as described under Example 1 were virtually inactive in preventing the development of disease symptoms. To the contrary, all enzymes applied at identical levels of esterase activity, as determined with the nonspecific esterase substrate p-nitrophenyl butyrate, gave full control of lesion development. As observed with cutinase before, small necrotic lesions indicated primary modes of action of the other esterases in the induction of host defense reactions.

The experiment also verified that the cutinolytic activities of respective esterases were not responsible for the observed effects in disease control. In comparison to the typical cutinase employed, cutinase activities of all other esterases at their active concentrations were >19-fold smaller. As described under Example 2, these low levels of cutinase activities were inactive in controling the disease. The experiment demonstrated that the esterase activities as assayed with the non-specific esterase substrate p-nitrophenyl butyrate and not the cutinase activities of the enzymes were responsible for the observed effects in the control of web blight disease.

TABLE 2

Development of web blight lesions on bean leaves infected with droplets containing mycelium of *Rhizoctonia solani* and various amounts of esterases.

| Enzyme | Percent of control[a] Protein[b] | PNBase[c] | Cutinase[d] |
|---|---|---|---|
| Cutinase | 100[e] | 100[e] | 39 |
| Lipase PS | 19 | 100[e] | 1 |
| Lipase AK | 10 | 100[e] | 2 |
| Carboxylesterase | 16 | 100[e] | 0 |

[a]Based on comparison of lesions diameters of nontreated controls; mean of 20 inoculation sites.
[b]Inoculation droplets (10 μl) contained 0.1 μg of enzyme.
[c]Inoculation droplets (10 μl) contained 1.75 nkat of esterase activity assayed with p-nitrophenyl butyrate.
[d]Cutinase activity (Bq/h) contained in infection droplets (10 μl) ammended with 1.75 nkat PNBase activity.
[e]Small necrotic lesions.

Example 3

Cuticle Decomposition at Disease-Controling Cutinase Concentrations

Esterases such as lipase and cutinase have been shown to improve the biological activities of fungicides and other pesticides by assuming a decomposition of the waxy outer layer (=cuticle) of plants as the cause for the reported effects (Iwasaki, T., and Hioki, Y. 1988. Enhancement of biocide. U.S. Pat. No. 4,762,547). This feature of cutinase at a concentration of 0.01 mg/ml, which was fully active in the control of disease (Example 2) was investigated by the uptake of a amino acid mixture into bean leaf tissue through intact, cutinase-treated and mechanically wounded cuticles. The rationale was to study potentially increased uptake of compounds normally restricted by the cuticular waxy layer as a cause for the esterase-mediated control of a plant disease described under Examples 1 and Example 2.

Bean leaves grown as described under Example 1 were excised. Surface areas for various treatments were deliniated from surrounding tissue with tygon rings (0.5 cm height, 1 cm diameter) attached to leaf surfaces with vaseline. The tygon troughs were filled with 0.3 ml of a solution containing 0.1% Tween 20 alone or containing 0.01 mg/ml cutinase. Treated leaves were incubated for 24 h as described under Example 1. Separate leaf sections were surface-wounded by rubbing the sections with carborundum and by deliniating the wounded area with vaseline-attached tygon rings. Carborundum was removed by filling the troughs with 0.3 ml of water, which was subsequently removed. The washing procedure was repeated three times.

The areas treated for 24 h with water or water containing cutinase in the presence of 0.1% Tween 20 were washed as described for carborudum-treted areas above in order to remove the incubation liquid. All washed sites were then exposed to 0.1 ml water each containing 20,000 Bq of a mixture of $^{14}C$-labeled amino acids for 60 min. The amino acid mixtures were removed, and the sites were washed four times with water as described above in order to remove amino acids remaining on the leaf surfaces and not penetrated into the leaf tissue. To investigate the efficacy of the washing procedure, the radioactive amino acid mixture was also applied to a sealed but untreated surface area followed by immediate removal and respective washing steps. The treated leaf sections were excised, solubilized in Protosol, and the radioactivity contained in respective leaf tissues was counted with a scintillation counter. Each treatment was repeated four times with randomly chosen surface areas on four different leaves. The results are summarized in Table 3.

The small amount of radioactivity found in leaf segments exposed to the amino acids followed by immediate removal and surface washes demonstrated that >95% of the radiocativity recovered in other treatments represented amino acids that had penetrated into the leaf tissue. The mechanical disruption of the cuticle with carborundum used as a mild abrasive had the most pronounced effect on the penetration of amino acids into leaf tissue. In comparison, treatment of waxy surfaces with cutinase at a concentration active in the control of web blight (Example 2) had only a negligible effect on the uptake of amino acids through the cuticular waxy layer. Statistical data analysis (ANOVA) showed that the slight increase over the water control was insignificant ($p=0.3$).

The result demonstrated that the observed effects of esterases in triggering plant defenses and, therefore, controling plant diseases described in Examples 1 and 2 were not related to the decomposition of waxy surface layers as described as the mechanism by which esterases enhance the activity of biocides (Iwasaki, T., and Hioki, Y. 1988. Enhancement of biocide. U.S. Pat. No. 4,762,547).

TABLE 3

Uptake of amino acids through cuticles of bean leaves.

| Treatment | Radioactivity[a] (Bq) |
|---|---|
| Surface-bound[b] | 9 |
| Surface wounded[c] | 2797 |
| Water | 323 |
| Water + cutinase | 561 |

[a]Mean of 4 sites.
[b]Application of amino acids immediately followed by washing.
[c]Carborundum Example 4

Control of White Mold with Cutinase

White mold of beans is caused by *Sclerotinia sclerotiorum* (Lib.) de Bary. The disease affects all aerial parts of beans and is often highly destructive (R. Hall, ed. 1991. Compendium of Bean Diseases, APS Press, St. Paul).

Infection of exised bean leaves was done as described for web blight in Example 1, with the exception of the pathogen. Infection droplets contained mycelial fragments of *Sclerotinia sclerotiorum* (field isolate obtained from Dr. H. R. Dillard, Cornell University).

As before, cutinase at a concentration of 0.035 mg/ml fully prevented disease symptom development, with small necrotic lesions typical for the induction of plant defenses appearing at infection sites treated with cutinase (Table 4).

TABLE 4

Development of white mold on bean leaves infected with droplets containing Sclerotinia sclerotiourum mycelium, 0.1% Tween 20, and various amounts of cutinase

| Cutinase concentration (mg/ml) | Lesions[a] |
|---|---|
| 0 | +++ |
| 0.010 | +++ |
| 0.035 | —[b] |

[a]+++, round water-soaked lesions; –, no expanding lesions.
[b]Small necrotic lesions.

Example 5

Control of Black Rot with Cutinase

Black rot caused by *Guignardia bildwellii* is an economically important disease of grapes in the northeastern United States, Canada, parts of Europe and South America (Pearson, R. C., and Goheen, A. C., eds. 1988. Compendium of Grape Dieseases. APS Press, St. Paul).

Infections of grape leaves with *Guignardia bildwellii* were done with shoots of grapevines (cv. Chadonney) propagated from shoot cuttings at 25 C. in the greenhouse. At the time of inoculation, the shoots contained 16 leafes, with LEAF 15 and LEAF 14 (counted from the bottom) most susceptible to the pathogen.

The two most susceptible leaves were treated with a aqueous solution containing cutinase at a concentration of 0.05 mg/ml and Tween 20 at a concentration of 0.1% (v/v) (=cutinase-treated). The solution (0.1 ml per leaf) was spread over the upper surfaces of respective leaves. Control leaves were treated accordingly, with a solution containing Tween 20 but no cutinase (=nontreated). The surfaces were dried for 6 h prior to inoculation with the pathogen.

The susceptible leaves of grapevine shoots were sprayed until runoff with a suspension of conidia in water. The conidial density was $2\times10^5$ conidia/ml. Conidia of *Guignardia bildwellii* (field isolate obtained from Dr. R. C. Pearson, Cornell University) were rinsed from mycelial cultures of the fungus after growth on potato dextrose agar for 10 days at 25 C. The inoculated shoots were enclosed in plastic bags for 24 h, and then kept in a greenhouse chamber at 25 C.

Figure 3A:
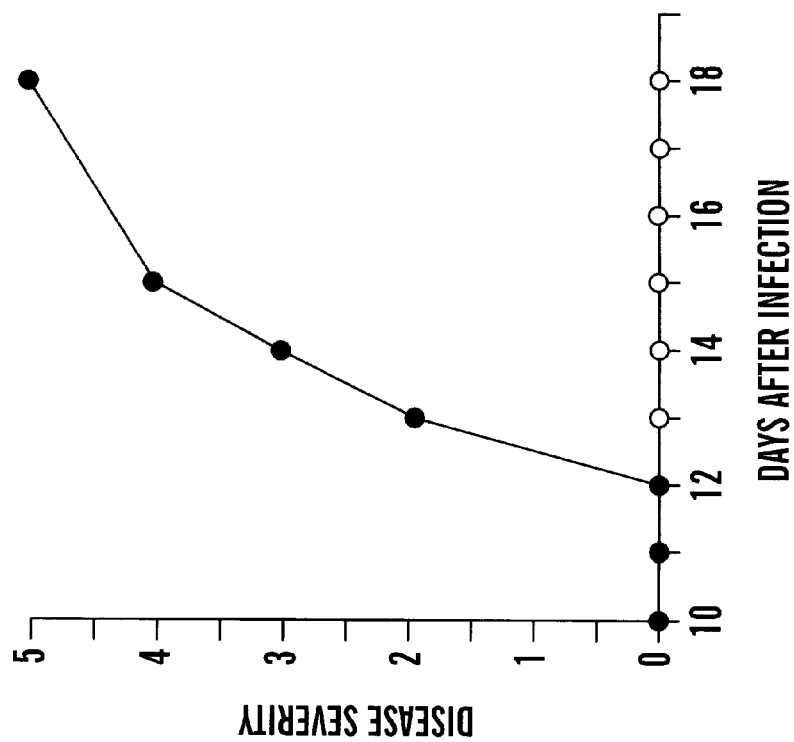
Figure 4:
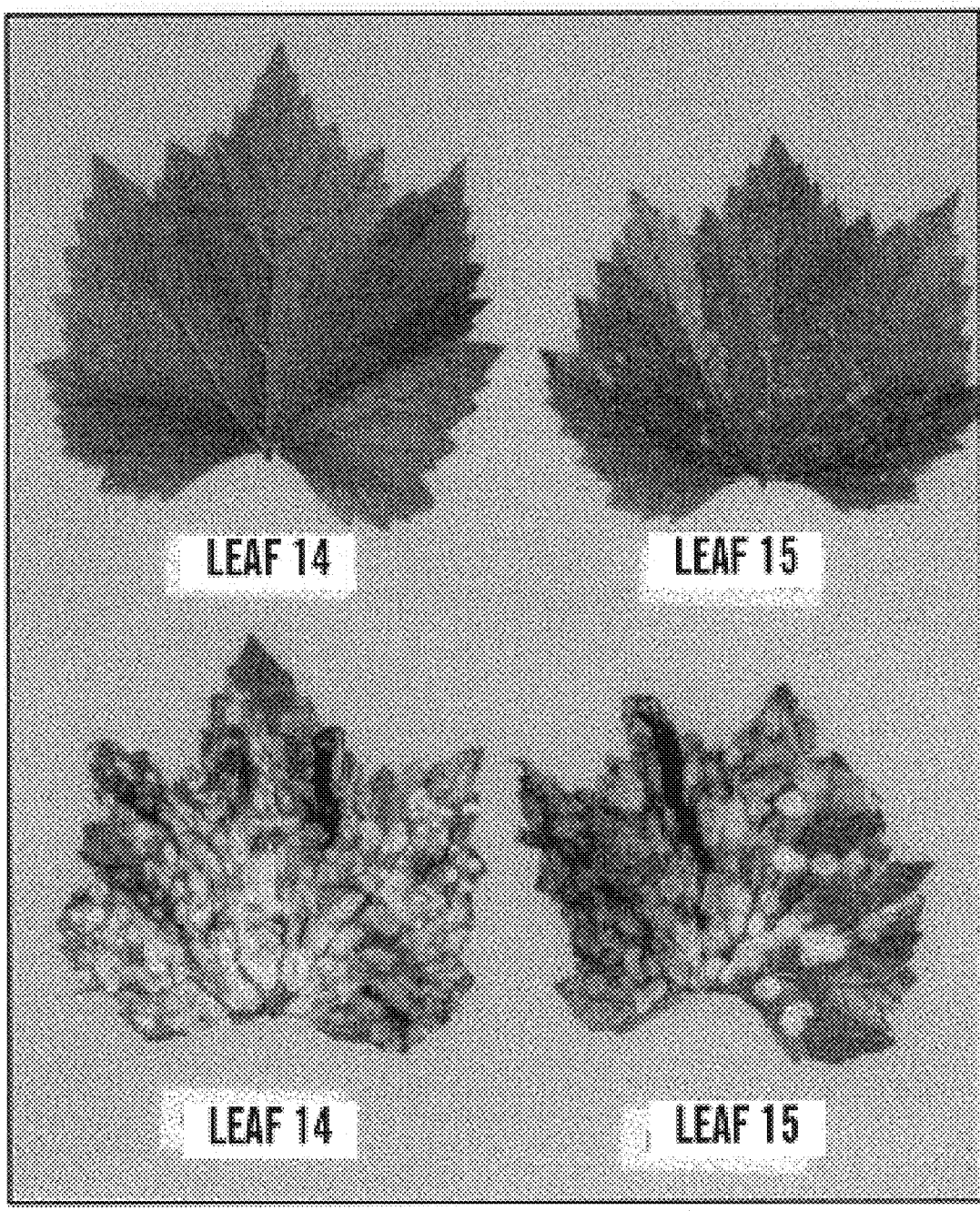
FIG. 4 shows symptoms of black rot on grape leaves 18 days after infection. Upper leaves: cutinase-treated. Lower leaves: nontreated controls.

Typically, disease symptoms in form of tan circular spots appeared 13 days after inoculation of nontreated leaves and expanded over the following 5 days (FIG. 3). No macroscopically visible symptoms or only very small necrotic lesions typical for plant defense reactions developed on leaves treated with cutinase (FIG. 3 and FIG. 4).

What is claimed:

1. A method for imparting disease resistance to plants comprising:
    applying a cutinase in the absence of another biocide to the cells of a plant, whereby resistance to plant diseases is imparted to the plant.
2. A method according to claim 1, wherein the plant is selected from the group consisting of dicots and monocots.
3. A method according to claim 2, wherein the plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

4. A method according to claim 2, wherein the plant is selected from the group consisting of *Arabidopsis thaliana, Saintpaulia petunia*, pelargonium, poinsettia, chrysanthemum, carnation, and zinnia.

5. A method according to claim 1, wherein the disease is fungal, viral, or bacterial.

6. A method according to claim 1, wherein said applying is carried out by spraying.

7. A method according to claim 1, wherein the cutinase is applied to plants as a composition further comprising a carrier.

8. A method according to claim 7, wherein the carrier is selected from the group consisting of water and aqueous solutions.

9. A method according to claim 8, wherein the cutinase is applied to plants as a composition further comprising a surfactant.

10. A method according to claim 1, wherein the cutinase is derived from Venturia.

11. A method according to claim 10, wherein the cutinase is derived from *Venturia inequalis*.

12. A method according to claim 1, wherein cutinase is applied to the plant in a concentration of less than 0.2 mg/ml.

13. A disease-resistant plant with cells in contact with a cutinase in the absence of another biocide, whereby resistance to plant diseases is imparted to the plant.

14. A plant according to claim 13, wherein the plant is selected from the group consisting of dicots and monocots.

15. A plant according to claim 14, wherein the plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

16. A plant according to claim 14, wherein the plant is selected from the group consisting of *Arabidopsis thaliana, Saintpaulia petunia*, pelargonium, poinsettia, chrysanthemum, carnation, and zinnia.

17. A plant according to claim 13, wherein the disease is fungal, viral, or bacterial.

18. A plant according to claim 13, wherein the cutinase is derived from Venturia.

19. A plant according to claim 18, wherein the cutinase is derived from *Venturia inequalis*.

* * * * *